(12) United States Patent
Mackool

(10) Patent No.: US 7,762,978 B2
(45) Date of Patent: *Jul. 27, 2010

(54) METHOD AND INSTRUMENTATION FOR COOLING A SURGICAL INCISION

(75) Inventor: Richard J. Mackool, Astoria, NY (US)

(73) Assignee: Alcon, Inc., Hünenberg (CH)

( * ) Notice: Subject to any disclaimer, the term of this patent is extended or adjusted under 35 U.S.C. 154(b) by 725 days.

This patent is subject to a terminal disclaimer.

(21) Appl. No.: 11/734,212

(22) Filed: Apr. 11, 2007

(65) Prior Publication Data

US 2007/0185448 A1    Aug. 9, 2007

Related U.S. Application Data

(63) Continuation of application No. 10/753,892, filed on Jan. 8, 2004, now Pat. No. 7,351,219.

(51) Int. Cl.
*A61B 17/20* (2006.01)
(52) U.S. Cl. .............................. 604/22; 604/35; 604/46
(58) Field of Classification Search ................... 604/22, 604/268, 164.01, 164.02, 164.06, 164.08, 604/171, 128, 524, 44, 35, 46; 606/171, 606/172, 167, 169; 433/91–96
See application file for complete search history.

(56) References Cited

U.S. PATENT DOCUMENTS

| 4,869,715 | A | 9/1989 | Sherburne |
|---|---|---|---|
| 5,464,389 | A | 11/1995 | Stahl |
| 5,725,495 | A | 3/1998 | Strukel et al. |
| 5,741,226 | A | 4/1998 | Strukel et al. |
| 5,743,871 | A | 4/1998 | Strukel et al. |
| 5,919,157 | A | 7/1999 | Strukel |
| 5,964,777 | A | 10/1999 | Drucker |
| 6,117,149 | A | 9/2000 | Sorensen et al. |
| 6,159,175 | A | 12/2000 | Strukel et al. |
| 6,238,400 | B1 | 5/2001 | Bays |
| 6,299,591 | B1 | 10/2001 | Banko |
| 6,340,355 | B1 | 1/2002 | Barrett |
| 6,428,501 | B1 | 8/2002 | Reynard |
| 6,491,709 | B2 | 12/2002 | Shama et al. |
| D478,383 | S | 8/2003 | Timm et al. |
| 6,712,797 | B1 | 3/2004 | Southern, Jr. |
| 7,014,629 | B2 | 3/2006 | Mackool |
| 7,351,219 | B2 * | 4/2008 | MacKool ..................... 604/22 |

\* cited by examiner

*Primary Examiner*—Nicholas D Lucchesi
*Assistant Examiner*—Laura A Bouchelle
(74) *Attorney, Agent, or Firm*—Hess Patent Law Firm; Robert J. Hess

(57) ABSTRACT

An infusion sleeve of an ultrasonic vibrating needle. The sleeve is collapsible and serrated or scalloped at a distal end. Fluid flows through a passage between the needle and the infusion sleeve in a direction from the proximal end of the sleeve to a distal end of the sleeve. Upon reaching the distal end, the fluid emerges by flowing across valley formations that are between peak formations of the distal end of the infusion sleeve. The peak formations abut the exterior of the incision so that the fluid flow cools tissue at the incision and the needle.

11 Claims, 2 Drawing Sheets

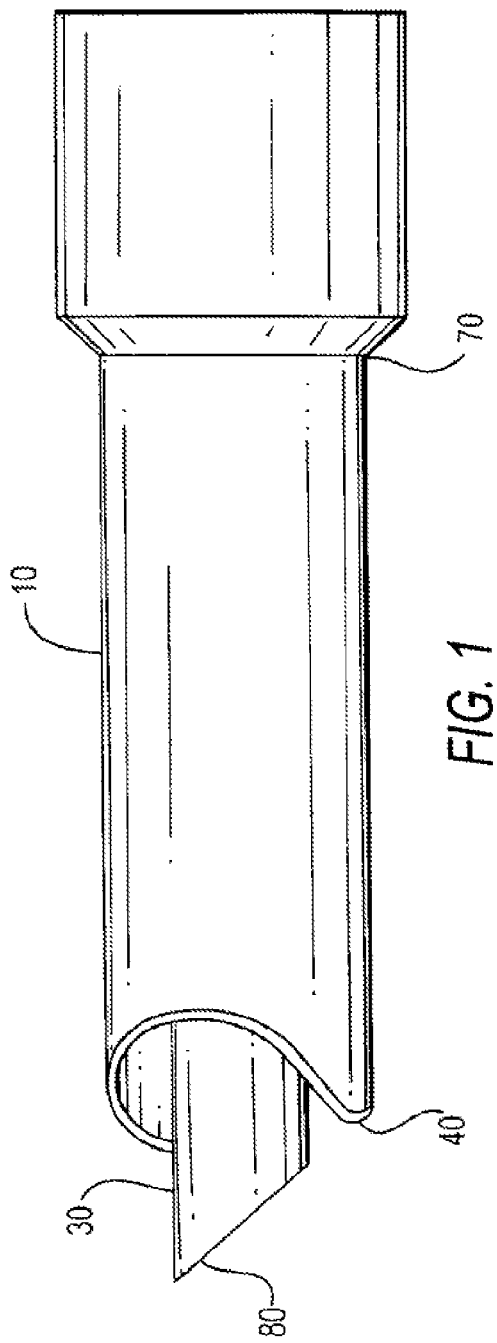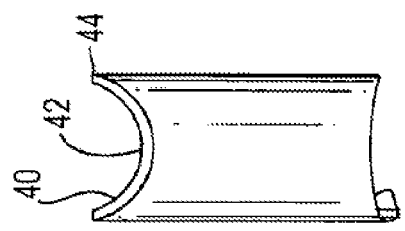

METHOD AND INSTRUMENTATION FOR COOLING A SURGICAL INCISION

CROSS-REFERENCE TO COPENDING PATENT APPLICATIONS

This is a continuation of U.S. patent application Ser. No. 10/753,892 filed Jan. 8, 2004 now U.S. Pat. No. 7,351,219.

BACKGROUND OF THE INVENTION

1. Field of the Invention

The invention relates to cooling a surgical incision in the human eye to prevent excessive temperature elevation within the incision from use of a vibrating, ultrasonic needle of a surgical instrument. Fluid flows through an infusion sleeve to travel across valley formations at the distal end of the sleeve to cool the incision.

2. Discussion of Related Art

A common method of cataract removal requires the use of a vibrating ultrasonic needle that can be inserted through a small incision in the human eye. The vibrating needle can cause temperature elevation within the incision. This temperature elevation is a problem that requires certain protective mechanisms, that is, precautions and/or technologies, in order to reduce the possibility of creating a thermal injury to the surrounding ocular tissues. Such protective mechanisms include the creation of an incision which is substantially larger than the ultrasonic needle or probe, with resultant leakage of fluid from the eye around the vibrating tip serving as a coolant. Other protective mechanisms include those previously devised by the applicant, and include the use of a rigid sleeve inserted between the vibrating needle and the soft, pliant outer sleeve through which infusion is delivered into the eye, or the use of an optical pachymeter to monitor the temperature in the vicinity of the ultrasonic needle or probe and discontinue needle or probe vibration in the event of undesirable temperature elevation.

Recently, there has been interest in performing ultrasonic removal (phacoemulsification) of human cataracts in a manner which divides the location of the entry of the infusion source and the ultrasonic needle into the eye into two smaller incisions in the eye. However, there has been concern that the use of a "bare" ultrasonic needle could increase the risk of thermal injury to the surrounding tissues because of the absence of surrounding infusion sleeves and the fluid contained within such infusion sleeve(s) that normally serve as coolants. It has therefore been advocated and it is the current practice to employ a method in which the surgical incision for insertion of the ultrasonic needle or probe be made substantially larger than that required for insertion of the needle or probe in order to permit fluid leakage from inside the eye to leak alongside the ultrasonic needle and thereby cool the latter.

While such a method will undoubtedly reduce the temperature of the needle, it is not desirable to have fluid leakage from the eye as this increases the trauma inflicted by fluid circulating through the eye during the procedure (a greater amount of fluid passes through the eye during the procedure), control of the pressure within the eye can be compromised by the leakage and this can lead to collapse of the eye, such collapse leading to contact of the vibrating ultrasonic needle with delicate ocular tissues such as the iris, cornea or lens capsule.

It has been the experience of applicant, who has performed tens of thousands of ultrasonic cataract extractions, that the greatest risk of thermal injury occurs at the external surface of the incision in the eye where such surface is in contact with the vibrating ultrasonic needle. This appears to be casually related to the fact that the environmental air is a poor conductor of heat away from the eye and the external tissues are therefore more likely to retain thermal energy transferred from the ultrasonic needle.

It would therefore be desired to provide a degree of cooling to the area of a surgical incision that is more rapid and efficient than that of air cooling to prevent a temperature rise at the incision to a medically unacceptable level during the use of a surgical device.

SUMMARY OF THE INVENTION

One aspect of the invention resides in an infusion sleeve whose end has peak and valley formations. The sleeve is collapsible and expandable axially. The needle defines an interior chamber and terminates at a tip. The infusion sleeve is hollow and elongated between proximal and distal ends. The needle extends within confines of the infusion sleeve. The tip projects outwardly beyond the distal end of the infusion sleeve. The infusion sleeve has an interior surface and the needle has an exterior surface between which is defined a passage for fluid flow. The distal end of the infusion sleeve has peak and valley formations. The valley formations are arranged closer to the proximal end of the infusion sleeve than are the peak formations. After the fluid flows through the passage by traveling in a direction to the distal end of the infusion sleeve and away from the proximal end of the infusion sleeve, the fluid flows across the valley formations to cool the incision.

The infusion sleeve abuts an exterior or external surface of the incision of the eye without entering the interior of the incision. The infusion sleeve collapses (shortens) or expands (elongates) as the needle is repetitively advanced and partially withdrawn through the incision.

BRIEF DESCRIPTION OF THE DRAWINGS

For a better understanding of the present invention, reference is made to the following description and accompanying drawing, while the scope of the invention is set forth in the appended claims:

FIG. 1 is a schematic representation of an infusion sleeve in accordance with the invention with the needle partially withdrawn.

FIG. 2 is a schematic representation one side of a distal portion of the infusion sleeve of FIG. 1.

FIG. 3 is a schematic representation of a further side of the distal portion of the infusion sleeve that is adjacent to the side shown in FIG. 2.

DESCRIPTION OF THE PREFERRED EMBODIMENT

Figure 4:
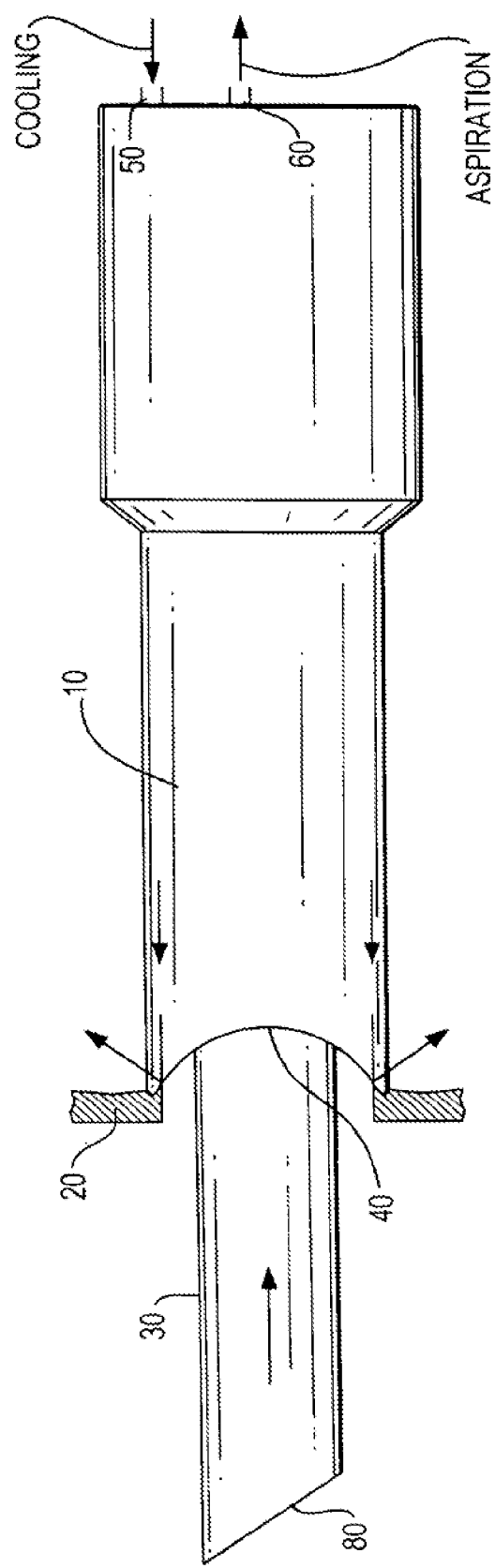
FIG. 4 is a schematic representation of fluid flows in accordance with the invention with the needle advanced and the infusion sleeve abutting an incision.

The present invention permits the needle to be inserted through a small incision and reduces the risk of thermal injury by providing a source of fluid to cool the area of the incision. It is intended that the small incision be used to aspirate material from the eye with the needle and that a separate incision be made to infuse fluid to irrigate the eye. Thus, unlike phacoemulsification instruments that aspirate and irrigate the eye through the same larger incision, the present invention envisions that two smaller incisions be used, one dedicated to irrigation of the eye and the other to aspirate the eye. The incision extends through eye tissue, which may be 1.5 to 2.5 mm in thickness. Thus, the needle would ordinarily travel more than 1 millimeter to reach the interior from the outside.

The needle is driven in a conventional manner at ultrasonic speeds to vibrate or oscillate, although the needle may alternatively be driven at higher or lower speeds within the meaning of the invention. While the tip of the needle is free to penetrate the interior of the eye, a portion of the needle spaced from the tip is within an infusion sleeve in accordance with the invention.

As shown in FIGS. 1 and 4, an infusion sleeve 10 is arranged to abut the external incision 20 but does not enter the incision. Such an infusion sleeve 10 may be made of extremely soft and pliant material so that it may collapse or expand, such as in an accordion-like manner. As the needle 30 repetitively advances (FIG. 5) and partially withdraws (FIG. 1) during performance of the surgical procedure, the infusion sleeve collapses in response to the needle being advanced and expands in response to the needle being partially withdrawn from the incision. For purposes of convenience of illustration, the portion of the distal end 40 of the infusion sleeve 10 that would normally be blocked from view by the protruding needle 30 is depicted in FIG. 1.

The distal end 40 of the sleeve may be scalloped or serrated (FIGS. 1-4) so that there is no impediment to the flow of fluid along the needle and over the external portion of the incision. Such flow will act to substantially cool the length of the needle and will also reduce the transmission of thermal energy distally along the needle shaft and eventually to the tissue surrounding the needle. In addition, such flow will also directly cool the tissues surrounding the incision.

In order to increase the beneficial cooling effect of the fluid, the fluid may be a liquid cooled by refrigeration prior to its actual use. Indeed, the rate of cooling and efficiency of heat transfer to the fluid flow is greater than that attained from the environmental air flow.

One or more spaces are between a distal end of the infusion sleeve and an external wall of the incision in the eye for allowing fluid flow as a result of the distal end being serrated or scalloped. These spaces form the valleys of the serrations or scallops, while the peaks of the serrations or scallops abut the exterior of the incision.

The needle need not be withdrawn automatically the full thickness of the tissue at the incision to receive the full benefit of cooling from the present invention even if a portion would overheat if allowed to linger. The reason is as follows. Consider the needle includes three portions: a proximal portion, an intermediate portion and a distal portion. The proximal portion is adjacent the exterior of the incision. The intermediate portion is proximate the interior of the incision and adjacent the proximal portion. The distal portion is clear of the tissue of the incision but adjacent the intermediate portion. It is assumed that the proximal portion is fully cooled by the infusion fluid of the present invention but the intermediate portion would not be if allowed to linger.

By partially withdrawing the needle 30 automatically, the intermediate portion becomes adjacent to the exterior of the tissue where the proximal portion used to be (because the proximal portion is moved clear of the exterior of the incision) and the distal portion moves adjacent the interior of the tissue where the intermediate portion used to be. In so doing, the intermediate portion has moved less than a full thickness of the tissue; it moves about one half or about one half a millimeter. However, it is now in a position be fully cooled by the infusion flow. While the distal portion is in a position to heat up the exterior of the tissue, upon advancing the needle further inwardly automatically, the distal portion clears the interior of the incision and the cooled intermediate portion once again become adjacent the interior of the incision where it may cool the tissue without lingering to heat it up because it will be partially withdrawn again before given a chance to do so.

The needle 10 is driven by a driver within a surgical handpiece to oscillate or vibrate at ultrasonic or subsonic speeds. The surgical handpiece has a cooling port 50 and a suction port 60. A suction source (vacuum) is connected to the cooling portion to suction through the interior chamber of the needle to provide aspiration. A refrigerated cooling fluid source is connected to discharge fluid through the infusion sleeve to cool the incision at the distal end 40 of the infusion sleeve 10.

At the distal end 40 of the infusion sleeve 10, the fluid flows across valley formations 42 but not across peak formations 44 that abut the exterior of the incision. The distal end 40 may have serrations or scallops that define the valley and peak formations. FIG. 4 includes flow arrows to show the direction of cooling fluid flow through a passage between the inner surface of the infusion sleeve 10 and the external surface of the needle 30 and across the valley formations 42 of the distal end 40. Flow arrows are also present to show the direction of aspiration flow through the internal chamber needle 30. The valley formations 42 are closer to the proximal end 70 of the infusion sleeve than are the peak formations 44. As the fluid flow travels across the valley formations 42, the exterior of the incision cools (FIG. 4). While such cooling of the incision takes place, the needle is driven to vibrate or oscillate while the needle tip 80 is aspirating the interior of the eye through the incision. The interior chamber of the needle and thereby the tip is in fluid communication with the suction source via the suction port 60.

The vibrating or oscillating of the needle tip is responsible for generating heat, either through rubbing contact with tissue at the incision or from heat caused by operation of the driver that vibrates or oscillates the needle. The cooling of the tissue from the fluid flow traveling across the valley formations helps prevent thermal damage to the tissue from arising that would otherwise result from the heat generation.

While the foregoing description and drawings represent the preferred embodiment of the present invention, it will be understood that various changes and modifications may be made without departing from the spirit and scope of the present invention.

What is claimed is:

1. A cooling apparatus, comprising a needle that defines an interior channel; and an infusion sleeve that is hollow and elongated between proximal and distal ends, the infusion sleeve being made of a flexible material and being collapsible and expandable axially while the needle is repetitively partially withdrawn and advanced, the needle extending within confines of the infusion sleeve and having a tip that projects outwardly beyond the distal end of the infusion sleeve, the infusion sleeve having an interior surface and the needle having an exterior surface between which is defined a passage for fluid flow, the infusion sleeve at the distal end terminating into peak and valley formations, the valley formations being arranged closer to the proximal end of the infusion sleeve than are the peak formations, the infusion sleeve being configured and arranged to prevent fluid flow across the peak formations while permitting the fluid flow across the valley formations after the fluid flow passes through the passage from the proximal end to reach the distal end so that the fluid flow changes direction of travel to pass across the valley formations.

2. The cooling apparatus of claim 1, wherein the distal end is serrated or scalloped to define the peak and valley formations.

3. The cooling apparatus of claim 1, wherein an infusion source is in fluid communication with the passage and a source of suction is in fluid communication with the interior channel of the needle.

4. The cooling apparatus of claim 1, further comprising a driver of the needle and a control that is configured to direct the driver to drive the needle without manual intervention to move axially relative to the infusion sleeve by a distance back and forth that is greater than that which the needle would otherwise travel.

5. The cooling apparatus of claim 1, wherein the infusion sleeve is configured and arranged to prevent fluid flow across the peak formations because of abutment of the peak formations with an incision.

6. A method of cooling, comprising extending a needle within confines of an infusion sleeve that is hollow and projecting a tip of the needle outwardly beyond a distal end of the infusion sleeve, the needle defining an interior channel, the infusion sleeve being elongated between the proximal and distal ends and being made of a flexible material that is collapsible and expandable axially as the needle is repetitively partially withdrawn and advanced, defining a passage between an interior surface of the infusion sleeve and an exterior surface of the needle, terminating the infusion sleeve at the distal end by peak and valley formations, arranging the valley formations closer to a proximal end of the infusion sleeve than are the peak formations, and preventing fluid flow across the peak formations while permitting the fluid flow across the valley formations after the fluid flow passes through the passage from the proximal end to reach the distal end so that the fluid flow changes direction of travel to pass across the valley formations.

7. The method of claim 6, wherein the distal end has serrations or scallops that define the peak and valley formations.

8. The method of claim 6, further comprising creating suction through the needle while the fluid flows to cool the needle.

9. The method of claim 6, wherein configuring the infusion source to be in fluid communication with the passage and arranging a source of suction in fluid communication with the interior channel of the needle.

10. The method of claim 6, further comprising repetitively expanding and collapsing the infusion sleeve as the needle repetitively advances and partially withdraws.

11. The method of claim 6, wherein the preventing arises from abutting the peak formations with an incision.

* * * * *